(12) United States Patent
Esser et al.

(10) Patent No.: US 6,191,285 B1
(45) Date of Patent: *Feb. 20, 2001

(54) PROCESS FOR THE PREPARATION OF KETOROLAC TROMETHAMINE

(75) Inventors: Grant L. Esser, Des Plaines; Marazban H. Vandrevala, Libertyville; Madhup K. Dhaon, Mundelein, all of IL (US); Ameen F. Ghannam, Oakland, CA (US); Dragan Obradovich, Kenosha, WI (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/206,474

(22) Filed: Dec. 7, 1998

Related U.S. Application Data

(63) Continuation-in-part of application No. 08/887,812, filed on Jul. 3, 1997, now abandoned.

(51) Int. Cl.⁷ .................................................. C07D 487/04
(52) U.S. Cl. ................................. 548/453; 203/56; 203/60
(58) Field of Search .............................. 548/453; 203/56, 203/60

(56) References Cited

U.S. PATENT DOCUMENTS

| | | | |
|---|---|---|---|
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,140,698 | 2/1979 | Van Horn et al. | 260/326.55 |
| 4,232,038 | 11/1980 | Kluge et al. | 424/274 |
| 4,344,943 | 8/1982 | Muchowski | 424/245 |
| 4,347,185 | 8/1982 | Muchowski et al. | 260/326.25 |
| 4,347,186 | 8/1982 | Muchowski et al. | 548/516 |
| 4,353,829 | 10/1982 | Thurber et al. | 260/326.25 |
| 4,454,151 | 6/1984 | Waterbury | 424/274 |
| 4,458,829 | 7/1984 | Greenfield, Jr. et al. | 222/129.3 |
| 4,496,741 | 1/1985 | Doherty | 548/453 |
| 4,835,288 | 5/1989 | Khatri et al. | 548/453 |
| 4,873,340 | 10/1989 | Muchowski et al. | 548/453 |
| 4,874,871 | 10/1989 | Fleming et al. | 548/543 |
| 4,937,368 | 6/1990 | Khatri et al. | 558/48 |
| 4,988,822 | 1/1991 | Muchowski et al. | 548/539 |

*Primary Examiner*—Robert W. Ramsuer
(74) *Attorney, Agent, or Firm*—Dugal S. Sickert

(57) ABSTRACT

The present invention provides an improved process for producing ketorolac tromethamine. The preferred method utilizes a three-part solvent system, comprising isopropanol, ethyl acetate and water.

31 Claims, No Drawings

PROCESS FOR THE PREPARATION OF KETOROLAC TROMETHAMINE

This application is a continuation-in-part of application Ser. No. 08/887,812, filed Jul. 3, 1997 now abandoned.

TECHNICAL FIELD OF THE INVENTION

This invention relates to a process for the preparation of ketorolac tromethamine.

BACKGROUND OF THE INVENTION

Ketorolac tromethamine has the following structure:

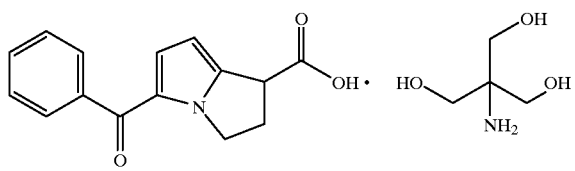

Ketorolac tromethamine is useful as an analgesic and anti-inflammatory agent. There exist a number of prior art methods for the production of amine salts of ketorolac, see, for example, U.S. Pat. Nos. 4,347,185 and 4,089,969. Typically these salts are prepared by solubilizing ketorolac acid and tromethamine in a nonpolar organic solvent and isolating the resulting tromethamine salt. However, these procedures rely on the low solubility of tromethamine in most nonpolar organic solvents, and results in inconsistent yields, incomplete salt formation, low potency, and inconsistent and unacceptable bulk densities of the final product.

For example, in U.S. Pat. No. 4,089,969, is disclosed a process for preparing amine salt derivatives of ketorolac acid wherein the process is conducted in a single or binary solvent system, i.e., in water, alone or in combination with an inert, water-miscible organic solvent. Exemplified is a process for preparing an amine salt of ketorolac acid where in the organic solvent utilized is benzene. However, benzene has the problem of being a carcinogen and therefore undesirable for use in preparing in a pharmaceutical product.

Alternate approaches have substituted acetonitrile as the reaction solvent and resulted in a product having good yields and high purity; however, like benzene, acetonitrile must be controlled at extremely low levels in the final product.

Further, such processes of the prior art yield lots of final product with inconsistent and unacceptable bulk densities. Bulk density is of great importance in preparing pharmaceutical products for oral administration, for example, when one considers the size of a high-dose capsule or the homogeniety of a low-dose formulation in which there are large differences in drug and excipient bulk densities. In addition, for the manufacture of solid dosage forms, it is desirable to have the bulk density in the range of about 0.3 to about 0.7 g/mL, or more preferrably about 0.35 to about 0.5 g/mL. The solid product obtained by such single or binary solvent distillation methods yields such product with such varied degree of bulk density that is not suitable or useful for oral formulations.

Thus there continues to be a need for improved methods for producing ketorolac tromethamine which provide a product of high quality and potency while avoiding undesirable solvents, and also yields a product of suitable bulk density for oral formulations.

BRIEF SUMMARY OF THE INVENTION

The present invention provides a process of producing ketorolac tromethamine in a three-part solvent system, i.e., in the presence of a lower alkyl alcohol, a lower alkyl acetate, and water. Because of the high solubility of tromethamine and ketorolac acid in the water/lower alkyl alcohol system, the addition of a lower alkyl acetate, increases the recovery of ketorolac tromethamine. As used herein, the term "lower alkyl" refers to a $C_1$–$C_4$ straight or branched, unsubstituted or substituted, alkyl chain. The solid product obtained by such a ternary distillation method yields product of consistent bulk density that is suitable for oral formulations.

In one aspect of the invention, ketorolac acid is dissolved in the lower alkyl alcohol. Tromethamine, previously dissolved in water, is mixed with the ketorolac acid solution. The binary mixture is placed under vacuum or atmospheric distillation. When approximately one-half of the volume of the mixture has been distilled, another portion of of the lower alkyl alcohol is added. Distillation is continued until approximately one-half the volume has been distilled. At this point, the lower alkyl acetate is added and the resulting mixture is again distilled until approximately half the volume is removed. The lower alkyl acetate distillation step is repeated again one or more times. After one-half the volume has been again distilled, the resulting mixture is cooled and the solid product is isolated by filtration.

Optionally, in a second aspect of the invention, the ketorolac acid is dissolved in the lower alkyl alcohol. Tromethamine, previously dissolved in water, is mixed with the ketorolac acid solution. To this mixture is added the lower alkyl acetate. The resulting ternary mixture is placed under vacuum or atmospheric distillation. When approximately one-half of the volume of the mixture has been distilled, another portion of of the lower alkyl acetate is added. Distillation is continued until approximately one-half the volume has been distilled. The lower alkyl acetate distillation step is repeated again one or more times. After one-half the volume has been again distilled, the resulting mixture is cooled and the solid product is isolated by filtration.

DETAILED DESCRIPTION OF THE INVENTION

The present invention relates to a process of producing ketorolac tromethamine which results in a product of consistently high quality and potency. Unlike the solvents used in the prior art, the solvents employed in the present invention are suitable for large scale processing, and give higher yields much more consistent bulk densities of final product. In addition, because of the high solubility of tromethamine and ketorolac acid in the water/isopropanol system, the quantities of solvents employed are minimized.

Ketorolac acid can be synthesized according to methods described in the following U.S. Pat. Nos. 4,087,539, 4,089, 969, 4,097,579, 4,140,698, 4,232,038, 4,344,943, 4,347,185, 4,347,186, 4,353,829, 4,454,151, 4,458,829, 4,835,288, 4,873,340, 4,874,871, 4,937,368, 4,988,822, and 4,496,741, the above incorporated by reference herein, or by other methods known to those skilled in the art.

The synthesis of ketorolac acid can be conveniently accomplished by treating a bicyclic nitrile compound (I)

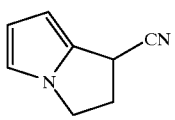

with N,N-dimethylbenzamide (the use of dimethylbenzamide being described in U.S. Pat. No. 4,344,943), to form 5-benzoyl-1,2-dihydro-3H-pyrrolo[1,2-a]pyrrole-1-nitrile. The nitrile is hydrolyzed to the corresponding acid as described in U.S. Pat. No. 4,353,829.

In accordance with the process of the invention, one aspect is described briefly here and in more detail below. One part ketorolac acid is dissolved in from three to twelve parts of a suitable solvent, typically a lower alkyl alcohol. Such preferred alcohols include ethanol, methanol, n-propanol, or, more preferably, isopropanol. Alternatively, ethers, e.g., tetrahydrofuran, can be employed. The preferred range is 4–8 parts solvent to one part ketorolac acid (w/w). In a separate container, one part tromethamine is dissolved in two to four, preferably two, parts water (w/w). The resulting mixture is combined with the ketorolac acid solution and mixed until a solution results. Alternatively, the ketorolac acid, solvent, tromethamine, and water can be combined in a single flask. The mixture is placed under vacuum distillation at a temperature of 20 to 60° C., or atmospheric distillation. When approximately one half of the volume has been distilled, conveniently determined by monitoring the volume of the distillate, a second portion of solvent, i.e., lower alkyl alcohol, equal to the remaining volume is added. Distillation is resumed under the conditions previously described and continues until approximately one half the volume has again been distilled. At this point an organic solvent, e.g., a lower alkyl acetate, preferably ethyl- or isopropyl acetate, etc., is added, and the resulting solution is again placed under distillation which continues until approximately half the volume is removed. Alternatively, toluene or xylene may be used as the third solvent. This step is repeated one or more times and distillation resumed until approximately half the volume has again been distilled. After half the volume has been distilled, the solution is cooled, preferably to −20 to +20° C. and the resulting solid product is isolated by filtration.

A second aspect of the invention is described briefly here and in more detail below. One part ketorolac acid is dissolved in from three to twelve parts of a suitable solvent, typically a lower alkyl alcohol. Such preferred alcohols include ethanol, methanol, n-propanol, or, more preferably, isopropanol. Alternatively, ethers, e.g., tetrahydrofuran, can be employed. The preferred range is 4–8 parts solvent to one part ketorolac acid (w/w). In a separate container, one part tromethamine is dissolved in two to four, preferably two, parts water (w/w). The resulting mixture is combined with the ketorolac acid solution and mixed until a solution results. To this mixture is added 10 to 16 parts, preferably 12 to 14 parts, of an organic solvent, e.g., a lower alkyl acetate, preferably ethyl- or isopropyl acetate, etc. Alternatively, the ketorolac acid, solvent, tromethamine, water, and organic solvent can be combined in a single flask. The mixture is placed under vacuum distillation at a temperature of 20 to 60° C., or atmospheric distillation. When approximately one half of the volume has been distilled, conveniently determined by monitoring the volume of the distillate, a second portion of organic solvent equal to the remaining volume is added. Distillation is resumed under the conditions previously described. This step is repeated one or more times and distillation resumed until approximately one half the volume has again been distilled. After half the volume has been distilled, the solution is cooled, preferably to −20 to +20° C. and the resulting solid product is isolated by filtration.

The following examples illustrate embodiments of the invention and are not limiting of the specification and claims in any way. All materials are reagent grade or better and are available from commercial vendors (e.g., Sigma Chemical Company St. Louis, Mo.; Aldrich Chemical Company, Milwaukee, Wis.)

EXAMPLE 1

Ketorolac acid (20 gm, Abbott Laboratories) was dissolved in 145 mL isopropanol. In a separate container, 10 gm of tromethamine (Aldrich Chemical Co.) was dissolved in 20 mL distilled water. The two mixtures were combined, mixed for 30 minutes then vacuum distilled under heat. Distillation was continued until approximately one half the volume remained, e.g., about 80 mL. Isopropanol (145 mL) was added and distillation continued until one half the volume remained, whereupon 270 mL of ethyl acetate was added and distillation of the ternary mixture continued. Upon removal of one-half the distillate, the ethyl acetate addition was repeated. When the volume was again brought to one half the starting volume, distillation was terminated. The solution was cooled to 10° C. and the solid ketorolac tromethamine isolated by filtration. The collected solids were dried under vacuum to afford 25 gm of the desired product. HPLC analysis showed purity of >99% of the desired compound.

EXAMPLE 2

Ketorolac acid (10.0 gm, Abbott Laboratories) is dissolved in 75 mL isopropanol. In a separate container, 5.0 gm of tromethamine (Aldrich Chemical Co.) is dissolved in 10 mL distilled water. The two mixtures are combined, mixed for 30 minutes then distilled under atmosphereric conditions. Distillation is continued until approximately one half the volume remains, e.g., about 40 mL. Isopropanol (72 mL) is added and distillation continued until one half the volume remains, whereupon 135 mL of ethyl acetate is added and distillation of the ternary mixture continued. Upon removal of one-half the distillate, the ethyl acetate addition is repeated. When the volume is again brought to one half the starting volume, distillation is terminated. The solution is cooled to 10° C. and the solid ketorolac tromethamine isolated by filtration. The collected solids are dried under vacuum to afford the desired product.

EXAMPLE 3

Ketorolac acid (20 gm, Abbott Laboratories) was dissolved in 156.0 gm of isopropanol. A solution of 12.0 gm of tromethamine in 25.0 gm of water was added, and the mixture was heated to 40° C. to a solution. The solution was filtered thru a 0.2 micron filter. To the clear filtrate was added 356.0 gm of ethyl acetate, and the ternary solution was distilled under atmospheric conditions to approximately half the volume. Another aliquot of 356.0 gm of ethyl acetate was added and the mixture distilled to approximately half the volume. At this point solid started precipitating out. Ethyl acetate (356.0 gm) was added once more and the mixture distilled to approximately half the volume. The solution was cooled to 10° C. and the solid ketorolac tromethamine was isolated by filtration. The collected solids were dried under vacuum to afford 36.1 gm of the desired product. HPLC analysis showed a purity of >99% of the desired compound.

EXAMPLE 4

Ketorolac acid (20 gm, Abbott Laboratories) is dissolved in 156.0 gm of isopropanol. A solution of 12.0 gm of tromethamine in 25.0 gm of water is added, and the mixture is heated to 40° C. to a solution. The solution is filtered through a 0.2 micron filter. To the clear filtrate is added 356.0 gm of ethyl acetate, and the ternary solution is distilled under vacuum to approximately half the volume. Another aliquot of 356.0 gm of ethyl acetate is added and the mixture distilled to approximately half the volume and solid starts precipitating out. Ethyl acetate (356.0 gm) is added once more and the mixture distilled to approximately half the volume. The solution is cooled to 10° C. and the solid ketorolac tromethamine is isolated by filtration. The collected solids are dried under vacuum to afford the desired product.

We claim:

1. A process for making ketorolac tromethamine comprising the steps of:
   a. combining a first solution comprising ketorolac acid in a suitable solvent with a second solution comprising tromethamine in water;
   b. distilling the resulting solution until about one half the volume remains;
   c. adding an amount of solvent equal to the volume remaining after step (b) and repeating step (b);
   d. adding an amount of organic solvent equal to the volume remaining after step (c) and repeating step (b);
   e. repeating step (d) one or more times;
   f. precipitating and collecting the ketorolac tromethamine.

2. The process of claim 1 wherein the ketorolac acid solution of step (a) comprises about three to twelve parts solvent to one part ketorolac acid (w/w).

3. The process of claim 2 wherein the solvent is selected from a lower alkyl alcohol or tetrahydrofuran.

4. The process of claim 3 wherein the solvent is selected from ethanol, methanol, n-propanol, isopropanol, and tetrahydrofuran.

5. The process of claim 4 wherein the solvent is isopropanol.

6. The process of claim 5 wherein the ratio of solvent to ketorolac acid is about 4–8:1 (w/w).

7. The process of claim 1 wherein the tromethamine solution of step (a) comprises about one part tromethamine to about two to four parts water (w/w).

8. The process of claim 7 wherein the ratio of tromethamine to water is 1:2 (w/w).

9. The process of claim 1 wherein the orgainc solvent of step (d) is a lower alkyl acetate.

10. The process of claim 9 wherein the lower alkyl acetate is selected from ethyl acetate and isopropyl acetate.

11. The process of claim 10 wherein the solvent is ethyl acetate.

12. A process for making ketorolac tromethamine comprising the steps of:
   a. combining a ketorolac acid in a lower alkyl alcohol with tromethamine in water;
   b. distilling the resulting solution under conditions of temperature and vacuum until about one half the volume remains;
   c. adding an amount of solvent equal to the volume remaining after step (b) and repeating step (b);
   d. adding an amount of lower alkyl acetate equal to the volume remaining after step (c) and repeating step (b);
   e. repeating step (d) one or more times;
   f. precipitating and collecting the ketorolac tromethamine.

13. A process for making ketorolac tromethamine comprising the steps of:
   a. combining ketorolac acid and isopropanol (1:4 to 8 (w/w)) with tromethamine in water (1:2 (w/w));
   b. distilling the resulting solution until about one half the volume remains;
   c. adding an amount of isopropanol equal to the volume remaining after step (b) and repeating step (b);
   d. adding an amount of ethyl acetate equal to the volume remaining after step (c) and repeating step (b);
   e. repeating step (d) one or more times;
   f. cooling the resulting distillate to 10° C. and collecting the ketorolac tromethamine by filtration.

14. A process of claim 13 wherein the distillation of step (b) is carried out under atmosperic conditions.

15. A process for making ketorolac tromethamine comprising the steps of:
   a. combining a first solution comprising ketorolac acid in a suitable solvent, with a second solution comprising tromethamine in water, and with a third solution comprising an organic solvent;
   b. distilling the resulting solution until about one half the volume remains;
   c. adding an amount of organic solvent equal to the volume remaining after step (b) and repeating step (b);
   d. repeating step (c) one or more times;
   e. precipitating and collecting the ketorolac tromethamine.

16. The process of claim 15 wherein the ketorolac acid solution of step (a) comprises about three to twelve parts solvent to one part ketorolac acid (w/w).

17. The process of claim 16 wherein the solvent is selected from ethanol, methanol, n-propanol, isopropanol, and tetrahydrofuran.

18. The process of claim 17 wherein the solvent is isopropanol.

19. The process of claim 18 wherein the ratio of solvent to ketorolac acid is about 4–8:1 (w/w).

20. The process of claim 15 wherein the tromethamine solution of step (a) comprises about one part tromethamine to about two to four parts water (w/w).

21. The process of claim 20 wherein the ratio of tromethamine to water is 1:2 (w/w).

22. The process of claim 15 wherein the organic solvent of step (a) is selected from a lower alkyl acetate.

23. The process of claim 22 wherein the lower alkyl acetate is selected from ethyl acetate and isopropyl acetate.

24. The process of claim 23 wherein the organic solvent is ethyl acetate.

25. A process for making ketorolac tromethamine comprising the steps of:
   a. combining a first solution comprising ketorolac acid in a lower alkyl alcohol, with a second solution comprising tromethamine in water, and with a third solution comprising a lower alkyl acetate;
   b. distilling the resulting solution until about one half the volume remains;
   c. adding an amount of said equal to the volume remaining after step (b) and repeating step (b);
   d. repeating step (c) one or more times;
   e. precipitating and collecting the ketorolac tromethamine.

26. A process for making ketorolac tromethamine comprising the steps of:
   a. combining ketorolac acid and isopropanol (1:4 to 8 w/w)), with tromethamine in water (1:2 w/w)), and with ethyl acetate (14 parts w/w)
   b. distilling the resulting solution until about one half the volume remains;
   c. adding an amount of ethyl acetate equal to the volume remaining after step (b) and repeating step (b);
   d. repeating step (co one or more times;
   e. cooling the resulting distillate to 10° C. and collecting the ketorolac tromethamine by filtration.

27. A process of claim 26 wherein the distillation of step (b) is carried out under atmospheric conditions.

28. A process of claim 25 wherein the bulk density of the final product is about 0.3 to 0.7 g/mL.

29. A process of claim 28 wherein the bulk density is about 0.35 to 0.5 g/mL.

30. A process of claim 26 wherein the bulk density of the final product is about 0.3 to 0.7 g/mL.

31. A process of claim 30 wherein the bulk density is about 0.35 to 0.5 g/mL.

* * * * *